United States Patent
Schapira et al.

[11] Patent Number: 6,090,984
[45] Date of Patent: Jul. 18, 2000

[54] α-PHENOXY-ALKANOLS, THEIR METHODS OF PREPARATION AND THEIR APPLICATIONS

[75] Inventors: Joseph Schapira, Paris; Jean-Claude Cheminaud, Herblay; Jean-Jacques Gasse, Gaillon; Vincent Schanen, Paris; Benoit Rondot, Levallois Perret; Jean-Claude Lemoine, Chatenay Malabry, all of France

[73] Assignee: CFPI Agro, France

[21] Appl. No.: 09/109,489

[22] Filed: Jul. 2, 1998

[30] Foreign Application Priority Data

Jul. 2, 1997 [FR] France .................................. 97 08361

[51] Int. Cl.[7] .................................................. C07C 205/19
[52] U.S. Cl. ............................................. 564/399; 568/587
[58] Field of Search ............................... 568/587; 564/399

[56] References Cited

U.S. PATENT DOCUMENTS 5,475,148 12/1995 Sarel .
5,602,283 2/1997 Sarel .

FOREIGN PATENT DOCUMENTS 0 630 883 6/1994 European Pat. Off. .
1 386 347 11/1963 France .

OTHER PUBLICATIONS

Journal of the American Chemical a Society, vol. 73, No. 9 Sep. 9, 1951, pp. 4162–4168, J.F. Kerwin et al.: "Adrenergic Blocking Agents. III N–(aryloxyisopropyl)–beta–haloethylamines."

B. Becker et al.: "Studien uber Phenoplaste" Monatshefte für Chemie, vol. 77, 1947, pp. 80–85.

Primary Examiner—Robert Gerstl
Attorney, Agent, or Firm—Jones & Askew LLP

[57] ABSTRACT

New α-phenoxy-alkanols represented by the general formula

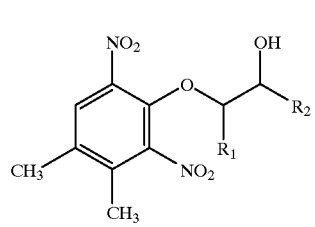

(I)

in which $R^1$ and $R_2$, which may be identical or different, represent a hydrogen atom or the $CH_3$ radical, and their stereoisomers of R,S conformation when they contain at least one asymmetric carbon.

10 Claims, No Drawings

α-PHENOXY-ALKANOLS, THEIR METHODS OF PREPARATION AND THEIR APPLICATIONS

The invention relates to new α-phenoxy-alkanols.

It also relates to a method of preparation of these new α-phenoxy-alkanols as well as their applications as synthetic intermediates, in particular for the preparation of pendimethalin, which is a selective herbicide belonging to the class of 2,6-dinitroanilines.

The new α-phenoxy-alkanols according to the invention and, when they contain at least one asymmetric carbon, their stereoisomers of R,S conformation, are represented by the general formula

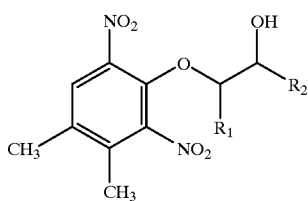

(I)

in which $R_1$ and $R_2$, which may be identical or different, represent a hydrogen atom or the $CH_3$ radical.

The process according to the invention for the preparation of α-phenoxy-alkanols of formula (I) is characterized in that 2,6-dinitro-3,4-dimethylphenol is reacted with a lower oxirane selected from the group comprising ethylene oxide, propylene oxide and 2,3-epoxybutane.

The 2,6-dinitro-3,4-dimethylphenol can be obtained by any known nitration technique from 3,4-dimethylphenol which is a commercial product.

Pendimethalin is prepared starting from 3,4-dimethyl-phenoxy-alkanol of formula (I), which can be obtained as indicated above.

To do this,
either the 2,6-dinitro-3,4-dimethyl-phenoxy-alkanol is submitted to an amination reaction, especially with the aid of 3-aminopentane,
or the 3,4-dimethyl-phenoxy-alkanol is submitted to a nitration reaction followed by a reaction of amination of the nitrated derivative thus formed, especially with the aid of 3-aminopentane.

The invention will be understood even better from the additional description that follows and non-limitative examples relating to advantageous embodiments.

The α-phenoxy-alkanols of formula (I) are prepared by means of the reaction of addition of a lower oxirane on 2,6-dinitro-3,4-dimethylphenol.

This addition reaction can be effected in an inert organic solvent.

The inert solvent in question is chosen advantageously from the group comprising the aliphatic alkanes, in particular hexane, heptane, octane, nonane and dodecane, chlorinated derivatives, especially dichloromethane, 1,2-dichloroethane, chloroform, trichloroethylene and tetrachloroethylene, the dialkyl ethers especially the diethyl- and dipropyl-ethers as well as the dibutyl-ethers, and preferably the aromatic solvents, especially benzene, toluene and xylene.

The amount of solvent used during the reaction is not critical.

Preferably, the addition reaction is carried out in the absence of solvent, and then greater productivity is obtained.

The addition reaction is carried out at a temperature selected in the range from −40 to 300° C., preferably from −20 to 200° C. and even more preferably from −10 to 150° C.

It can be carried out at atmospheric pressure or under autogenous oxirane pressure.

It is preferably carried out under partial oxirane pressure controlled by the introduction of an inert gas, and more especially under controlled pressure of argon or nitrogen.

The reaction is preferably carried out under a total pressure from 1 to 100 atmospheres, more preferably from 1 to 25 atmospheres and, even more preferably, under a total pressure less than 10 atmospheres.

The molar quantities of oxirane employed in relation to the phenol used are in ratios of from 1 to 100, preferably from 1 to 20 and, even more preferably, from 1 to 5.

Preferably, the quantity of oxirane used is from 1 to 10 mol/mol of phenol, more preferably from 1 to 2 mol/mol and, even more preferably, from 1 to 1.2 mol/mol.

The reaction can be carried out in the absence of catalyst or in the presence of acid catalysts; preferably, a basic catalyst is employed, selected from the group comprising the tertiary aliphatic amines and especially from the group comprising trimethylamine, methyldiethylamine and triethylamine, the tertiary anilines especially dimethylaniline and diethylaniline, the cyclic amines especially pyridine and the imidazoles; it is also possible to employ alkaline bases, especially soda, potash and lime.

The catalyst is used in catalytic amounts, i.e. amounts by weight relative to the weight of phenol used from 10 ppm to 10000 ppm and preferably from 50 to 1000 The conditions of the addition reaction are maintained for a necessary and sufficient time to achieve a degree of conversion of the phenol greater than 99%; when a higher degree of purity is demanded, the reaction time can be extended accordingly without causing any deterioration of the quality of the α-phenoxy-alkanol formed.

The α-phenoxy-alkanols thus obtained have purity above 99%, necessary and sufficient to permit the preparation, in the embodiment according to the invention, of a commercial pendimethalin of purity above 97% and free from nitrosamines; in this preparation of pendimethalin, any known technique of nucleophilic substitution can be employed.

The α-phenoxy-alkanols according to the invention and represented by formula (I) can thus be synthesized easily and advantageously starting from commercial or readily accessible phenolic derivatives.

These α-phenoxy-alkanols are important intermediates for the economical and advantageous synthesis of the selective herbicide consisting of pendimethalin.

Another application of these α-phenoxy-alkanols is based on the fact that they can be used in the preparation of 2,6-dinitro-3,4-dimethylanilines which are important synthetic intermediates, by reaction with ammonia, a primary amine or a secondary amine.

The preparation of α-2,6-dinitro-3,4-dimethyl-phenoxy-propanol and its use for the preparation of pendimethalin can be represented by the following reaction schemes:

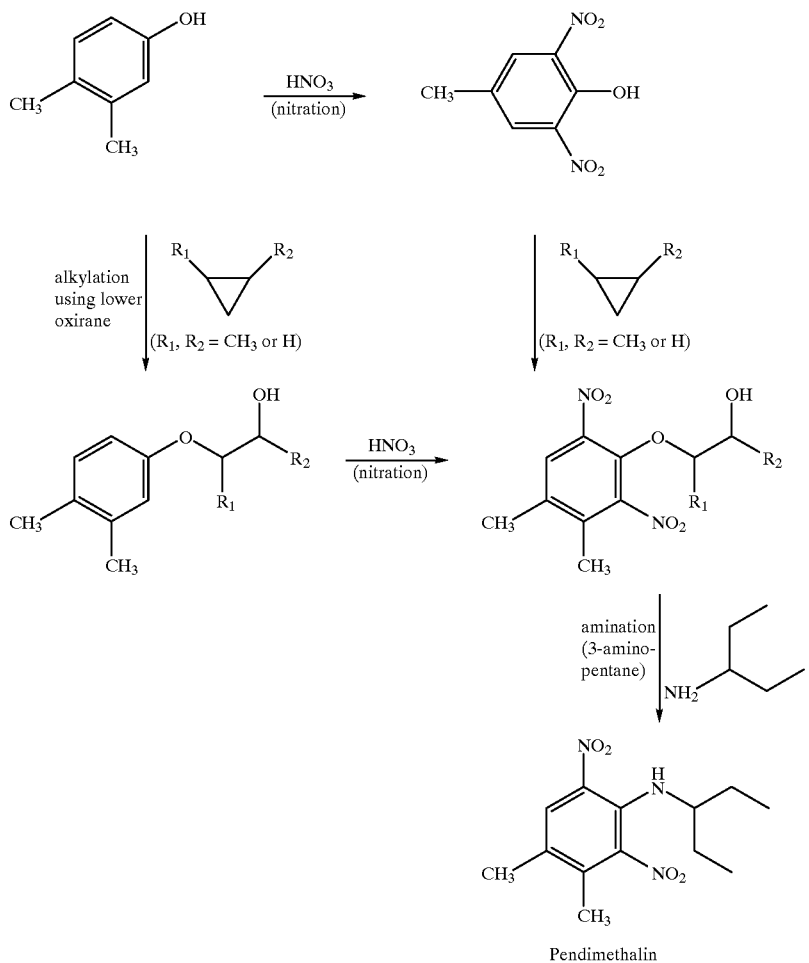

Pendimethalin

EXAMPLE 1
Preparation of an α-phenoxy-alkanol of formula (I).

A 100-ml autoclave is loaded with 4 g (18.8 mmol) of 99.9% 2,6-dinitro-3,4-dimethylphenol; 2.21 g (38 mmol) of 99% 1,2-epoxypropane and 3 drops of basic catalyst are introduced. Close the apparatus and pressurize to 3 bar of nitrogen pressure. Then raise the temperature to 100° C.; the reaction is monitored using thin-layer chromatography; after holding at 100° C. for 3 hours, the amount of residual phenol is less than 1% and the reaction is stopped.

Cool the reactor to room temperature, depressurize it and 5.10 g (100% yield) of a brownish red product is collected, consisting of
- 70% of 1-(2,6-dinitro-3,4-dimethyl-phenoxy)-2-propanol and
- 30% of 2-(2,6-dinitro-3,4-dimethyl-phenoxy)-1-propanol.

These two isomers are not separated as they are both precursors of pendimethalin.

EXAMPLE 2
Use of an α-phenoxy-alkanol of formula (I) in the preparation of pendimethalin.

Place 26.0 g (97.0 mmol) of the mixture of the two α-(2,6-dinitro-3,4-dimethyl-phenoxy)-propanol prepared according to example 1, in a 50-ml three-necked flask equipped with a stirrer, a thermometer, a reflux condenser and a pouring funnel, then introduce 59.5 g (687 mmol) of 3-aminopentane in the space of 10 minutes.

Leave to react for 14 hours at 90° C. under reflux; the progress of the reaction is monitored by thin-layer chromatography; after the ether has disappeared, the reaction is stopped.

The unreacted excess of amino-3-pentane is distilled at atmospheric pressure, passing at 90° C. under atmospheric pressure, which once recovered can be recycled for a further amination operation.

Then charge 100 ml of xylene and, after two hot washings with 50 ml of water, distil the xylene under reduced pressure.

After complete evaporation of the xylene, 26.4 g (i.e. 95% yield) of pendimethalin of 97% purity is collected.

EXAMPLE 3
Use of an α-phenoxy-alkanol of formula (I) in the preparation of pendimethalin.

Place 25.0 g (92.5 mmol) of the mixture of the two α-(2,6-dinitro-3,4-dimethyl-phenoxy)-propanol prepared according to example 1 in a 100-ml stainless steel autoclave equipped with a stirrer and a thermometer, then introduce a quantity of 40.3 g (462 mmol) of 3-aminopentane at 90° C. in the space of 30 minutes.

Leave to react under a pressure of 2 atmospheres for 3 hours at 90° C., then for 2 hours at 100° C., and finally for 3 hours at 130° C.; the progress of the reaction is monitored by thin-layer chromatography; after the ether has disappeared, the reaction is stopped.

Depressurize the reactor, then by distillation at atmospheric pressure, separate the unreacted excess of amino-3- pentane; the latter passes at 90° C. and can be recycled in a subsequent operation.

Then load 100 ml of xylene in the reaction vessel, wash hot twice with 50 ml of water, then distil the xylene under reduced pressure.

After complete evaporation of the xylene, 26.4 g (i.e. 98% yield) of pendimethalin of 96.4% purity is collected.

We claim:

1. New α-phenoxy-alkanols represented by the general formula

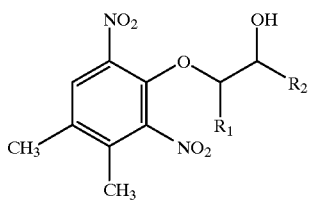

(I)

in which $R_1$ and $R_2$, which may be identical or different, represent a hydrogen atom or the $CH_3$ radical, and their stereoisomers of R,S conformation when they contain at least one asymmetric carbon.

2. A process for preparation of the α-phenoxy-alkanols according to claim 1, characterized in that 2,6-dinitro-3,4-dimethylphenol is reacted with a lower oxirane selected from the group comprising ethylene oxide, propylene oxide and 2,3-epoxybutane.

3. A process according to claim 2, characterized in that it is carried out at a temperature chosen in the range from −40 to 300° C., preferably from −20 to 200° C. and even more preferably from −10 to 150° C.

4. A process according to claim 2, characterized in that it is carried out under a total pressure of 1 to 100 atmospheres, more preferably from 1 to 25 atmospheres and, even more preferably, under a total pressure of less than 10 atmospheres.

5. A process according to claim 2, characterized in that the molar amounts of oxirane employed relative to the phenol used are in ratios of from 1 to 100, preferably from 1 to 20 and, even more preferably, from 1 to 5.

6. A process according to claim 2, characterized in that it is carried out in the presence of a basic catalyst selected from the group comprising the aliphatic tertiary amines and especially from the group comprising trimethylamine, methyldiethylamine and triethylamine, the tertiary anilines and especially dimethylaniline and diethylaniline, the cyclic amines and especially pyridine and the imidazoles.

7. A process according to claim 6, characterized in that the catalyst is employed at the rate of 10 ppm to 10000 ppm and preferably at the rate of 50 to 1000 ppm.

8. A process according to claim 2, characterized in that it is carried out in the absence of solvent.

9. A process according to claim 2, characterized in that it is carried out in an inert organic solvent selected from the group comprising the aliphatic hydrocarbons and especially hexane, heptane, octane, nonane and dodecane, the chlorinated derivatives and especially dichloromethane, 1,2-dichloroethane, chloroform, trichloroethylene and tetrachloroethylene, the dialkyl-ethers and especially diethyl- and dipropyl-ethers as well as the dibutyl-ethers, and preferably the aromatic solvents and especially benzene, toluene and xylene.

10. A method for the preparation of pendimethalin comprising reacting an α-phenoxy-alkanol of claim 1 with 3-aminopentane.

* * * * *